(12) United States Patent
Krueger et al.

(10) Patent No.: US 7,459,919 B2
(45) Date of Patent: Dec. 2, 2008

(54) DEVICE FOR CHECKING LIGHT-METAL PARTS

(75) Inventors: Juergen Krueger, Bremen (DE); Gerhard Scheer, Garbsen (DE)

(73) Assignee: Airbus Deutschland GmbH, Hamburg (DE)

( * ) Notice: Subject to any disclaimer, the term of this patent is extended or adjusted under 35 U.S.C. 154(b) by 0 days.

(21) Appl. No.: 11/982,712

(22) Filed: Nov. 2, 2007

(65) Prior Publication Data

US 2008/0129318 A1 Jun. 5, 2008

(30) Foreign Application Priority Data

Nov. 2, 2006 (DE) .................. 10 2006 051 573

(51) Int. Cl.
*G01R 27/08* (2006.01)
(52) U.S. Cl. .................. 324/693; 324/671; 324/674; 324/71.2
(58) Field of Classification Search .................. 324/693
See application file for complete search history.

(56) References Cited

U.S. PATENT DOCUMENTS

| | | | |
|---|---|---|---|
| 5,138,269 A | | 8/1992 | Deutsch |
| 5,221,893 A | * | 6/1993 | Kondou et al. ............. 324/71.2 |
| 5,532,606 A | * | 7/1996 | Descamps .................. 324/674 |
| 5,602,486 A | * | 2/1997 | Novak ........................ 324/671 |
| 5,859,537 A | * | 1/1999 | Davis et al. .................. 324/693 |
| 5,923,259 A | * | 7/1999 | Lederer ....................... 340/605 |
| 6,054,038 A | * | 4/2000 | Davis et al. ............... 205/776.5 |
| 2003/0122558 A1 | * | 7/2003 | Hacke .......................... 324/693 |
| 2008/0122459 A1 | * | 5/2008 | Krueger ........................ 324/693 |
| 2008/0150555 A1 | * | 6/2008 | Wang et al. .................. 324/693 |

* cited by examiner

*Primary Examiner*—Vincent Q Nguyen
*Assistant Examiner*—Benjamin M Baldridge
(74) *Attorney, Agent, or Firm*—Jenkins, Wilson, Taylor & Hunt, P.A.

(57) ABSTRACT

A device for checking the coating of anodized light-metal parts (e.g. Aluminum), in particular by TSA anodization, is described. The device has two contact electrodes on respective resilient probes, placed onto the surface of the component to be tested under a predefined contact pressure; an enabling device coupled to the probes that generates an enable signal when the predefined contact pressure is reached; and a conductivity measuring device coupled to the contact electrodes that measures the conductivity of the surface of the component under test.

The conductivity measuring device is coupled to the enabling device to detect the enable signal. When the enable signal is detected, the conductivity measuring device measures the surface conductivity of the component under test between the contact electrodes and generates an output signal indicating the measured conductivity. The device distinguishes between a measured low conductivity value, signifying a correct coating, and a measured high conductivity value, signifying a lack of the coating.

19 Claims, 2 Drawing Sheets

DEVICE FOR CHECKING LIGHT-METAL PARTS

CROSS-REFERENCE TO RELATED APPLICATIONS

This application claims the benefit of German Application No. 10 2006 051 573.0-52, filed Nov. 2, 2006, the entire disclosure of which is herein incorporated by reference.

FIELD OF THE INVENTION

The invention relates to a device for checking the coating of light-metal parts, in particular aluminum components, which have been coated by anodization, in particular by TSA anodization.

BACKGROUND OF THE INVENTION

Conventionally, it is known practice to provide light-metal parts, in particular aluminum components, which are used in large quantities in aircraft construction, with a protective layer by means of anodization. During chromic acid anodization (CAA=Chromatic Acid Anodizing), a protective layer which can be visually detected in a simple manner is produced, said layer having a "grey" appearance, while the surface of parts which have not been anodized have a "shiny" appearance. However, for reasons of better environmental compatibility, it is desirable to anodize parts of the type mentioned in another manner. An alternative anodization method is the TSA (Tartaric-Sulphuric Acid) method. As regards the corrosion protection required, this method is at least equal to the abovementioned chromic acid anodization but the layer formed cannot be visually detected.

SUMMARY OF THE INVENTION

It is an object of the present invention to provide a device for checking components which have been coated by anodization, said device being able to be used as simply as possible and requiring only a short test time.

This is achieved by means of a device having the features of claim 1. Advantageous embodiments and developments of the device according to the invention are characterized in the subclaims.

The invention provides a device for checking the coating of light-metal parts, in particular aluminum components, which have been coated by anodization, in particular by TSA anodization. The invention provides for the device to have two contact electrodes, which are arranged on respective resilient probes and are intended to be placed onto the surface of the component to be tested under a predefined contact pressure, as well as an enabling device, which is coupled to the probes and generates an enable signal when the predefined contact pressure is reached, and also a conductivity measuring device which is coupled to the contact electrodes in order to measure the conductivity of the surface of the component to be tested, is coupled to the enabling device in order to pick up the enable signal, measures the conductivity of the surface of the component to be tested between the contact electrodes and, when the enable signal is present, generates an output signal which indicates the measured conductivity and distinguishes at least between a measured low conductivity value, which signifies a correct coating, and a measured high conductivity value, which signifies a lack of the coating.

According to one embodiment of the invention, the enabling device contains switching devices which are coupled to the resilient probes and are respectively switched when the predefined contact pressure is reached, the enabling device generating the enable signal when both switching devices have been switched.

According to one embodiment, the probes are mounted or formed in a resiliently flexible manner and are coupled to the switching devices in such a manner that the switching devices are switched when the predefined contact pressure is reached.

According to another embodiment, the switching devices are formed in a resiliently flexible manner, are coupled to the probes and are switched when the predefined contact pressure is reached.

The switching devices may contain electrical switching contacts.

The switching devices may contain strain gauges.

The switching devices may contain piezo elements.

The switching devices may contain optical sensors.

The switching devices may also contain magnetic, inductive or capacitive sensors.

One embodiment of the invention provides for the measuring device to be provided for the purpose of generating an acoustic output signal which indicates the measured conductivity.

In this case, the measuring device may be provided for the purpose of generating the acoustic output signal with a pitch which differs depending on the measured conductivity.

According to one embodiment of the invention, the measuring device may be provided for the purpose of using a low tone to indicate a low conductivity, which signifies a correct coating, and using a high tone to indicate a high conductivity, which signifies a lack of the coating.

Additionally or alternatively, the measuring device may be provided for the purpose of generating an optical output signal which indicates the measured conductivity.

Additionally or alternatively, the measuring device may also be provided for the purpose of generating an electrical output signal which indicates the measured conductivity.

According to one embodiment of the invention, the device is provided in the form of an instrument which can be manually operated and has a handle for its handling.

The device may have its own current source.

BRIEF DESCRIPTION OF THE DRAWINGS

The present invention is explained in more detail below by way of exemplary embodiments and with reference to the attached figures of the drawings, in which.

Like reference numbers denote like items in the various figures.

DETAILED DESCRIPTION OF THE INVENTION

Figure 1:
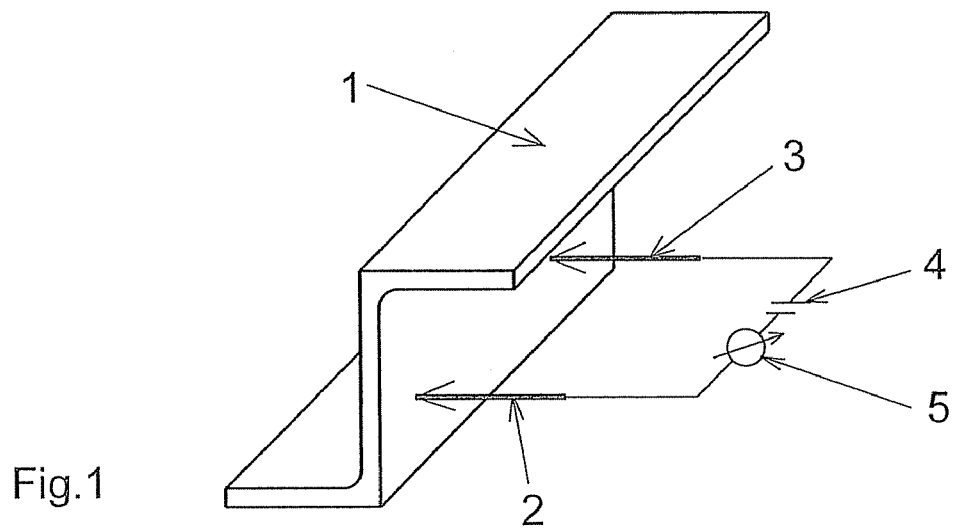
FIG. 1 shows a schematic perspective view of a component whose coating is to be checked, as well as a measuring device provided for this purpose, in a highly simplified illustration in accordance with one exemplary embodiment of the invention.

FIG. 1 shows a component 1 which has been provided with a coating by anodization, in particular by TSA anodization. The component 1 may be a light-metal part, in particular an aluminum component, which is used in large quantities in aircraft construction, for example.

Figure 2:
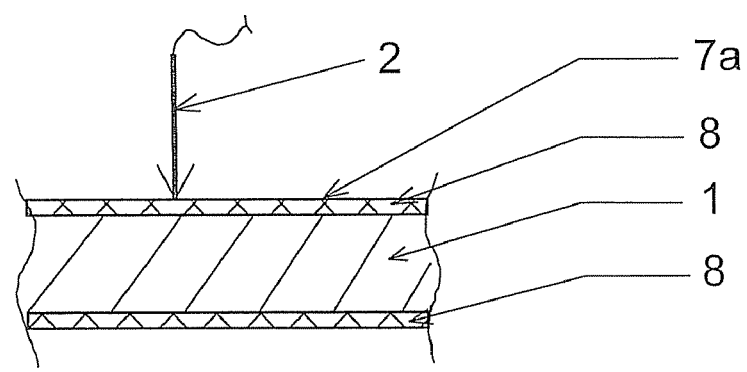
FIGS. 2a) and b) show an enlarged perspective cross-sectional illustration showing the component to be checked with a correct coating and a lack of the coating.
Figure 2:
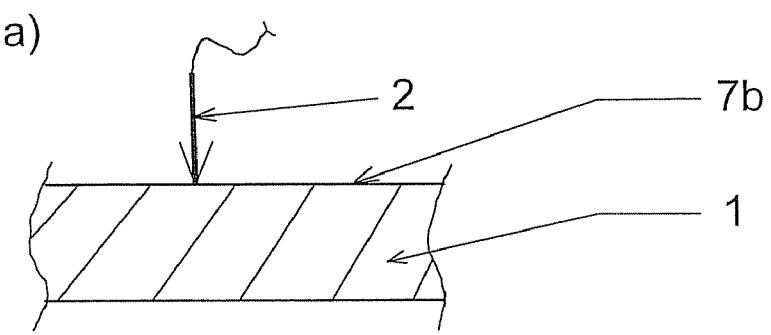

FIG. 2a) shows a cross section of an anodized layer 8 which has been correctly applied to the component 1 and is missing in the cross section shown in FIG. 2b) on account of a defect, for example defective or absent contact-connection during anodization.

In order to check the anodized layer, the surface resistance is measured at the surface 7a or 7b of the component 1, and the coating 8 is found to be good if the surface resistance is higher than a predefined high resistance value or the conductivity is lower than a predefined low conductivity value. In the case of a correct coating which has been produced by TSA anodization, the resistance is practically "infinite", that is to say the conductivity is practically zero.

Figure 3:
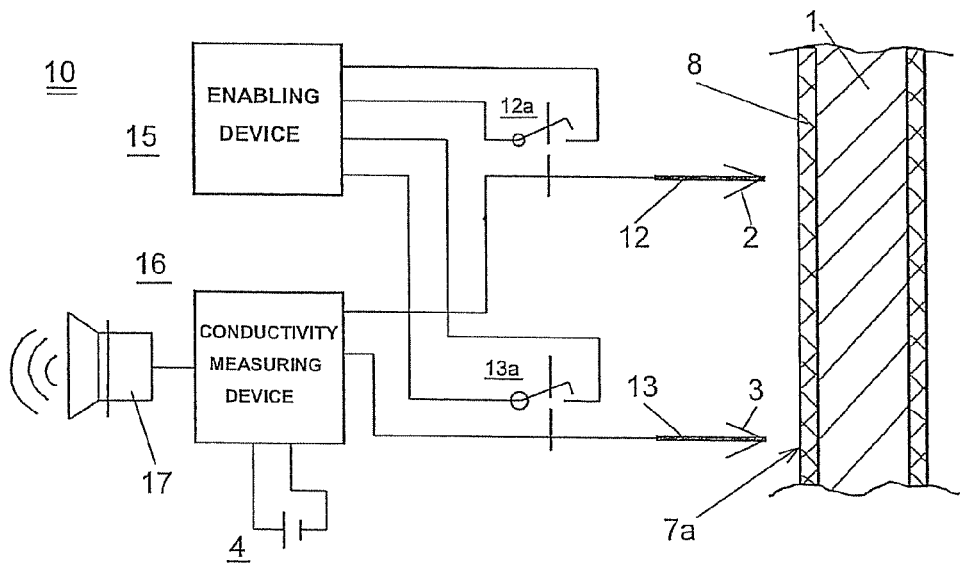
FIG. 3 shows a schematic circuit diagram of a device for checking the coating in accordance with the exemplary embodiment of the invention.

The device which is shown in a schematic circuit diagram in FIG. 3 and is intended to check the anodized layer 8 has two contact electrodes 2, 3 which are arranged on respective probes 12, 13. The probes 12, 13 are resilient. The contact electrodes 2, 3 are intended to be placed onto the surface of the component 1 to be tested under a predefined contact pressure which ensures that good electrical contact is established between the electrodes 2, 3 and that surface 7a or 7b of the component 1 which is to be tested. An enabling device 15 is coupled to the probes 12, 13, said enabling device generating an enable signal when the contact pressure predefined for correct measurement is reached.

A conductivity measuring device 16 is provided for the purpose of measuring the conductivity of the surface 7a, 7b of the component 1 to be tested, said conductivity measuring device measuring the conductivity of the component 1 between the contact electrodes 2, 3 and generating an output signal which indicates the measured conductivity when the enable signal from the enabling device 15 is present. In the schematic illustration of FIG. 1, the measuring device 16 is shown using a current source 4 and a current measuring instrument 5 which is connected in series with the current source 4 in a closed circuit by means of the contact electrodes 2, 3 and the component 1 to be tested. However, this is only a simplified illustration which is intended to illustrate the principle.

The conductivity measuring device 16 generates an output signal which distinguishes at least between a measured low conductivity value, which signifies a correct coating 8, and a measured high conductivity value, which signifies a lack of coating 8, as shown in FIGS. 2a) and 2b).

The measuring device 16 of the exemplary embodiment described here is provided for the purpose of generating an acoustic output signal which indicates the measured conductivity. The acoustic output signal which is generated using an acoustic converter 17 has a different pitch depending on the measured conductivity, namely a low tone in the case of low conductivity, which signifies a correct coating 8, said low tone being able to be at a frequency of 800 Hz, for example, and a high tone in the case of high conductivity, which signifies a lack of the coating 8, the high tone being able to be at a frequency of 4000 Hz, for example.

Additionally or alternatively, the measuring device 16 may also output an optical output signal as an indication of the measured conductivity or an electrical output signal. The electrical output signal may be logged, for example, in a data processing device if a large number of parts are measured.

The enabling device 15 has switching devices 12a, 13a which are coupled to the probes 12, 13 and are respectively switched when the contact pressure predefined for reliable contact-connection is reached, and the enabling device 15 generates said enable signal when both switching devices 12a, 13a have been switched, that is to say both contact electrodes 2, 3 are reliably resting on the component 1.

The probes 12, 13 are mounted or formed in a resiliently flexible manner and/or the switching devices 12a, 13a are formed in a resiliently flexible manner in such a way that the switching devices 12a, 13a which are coupled to the probes 12, 13 are switched when the predefined contact pressure is reached and said enable signal is thus generated. The probes 12, 13 may be longitudinally or transversely resilient or a combination thereof, and the contact electrodes 2, 3 may be arranged in the region of the tips of the probes 12, 13 in such a manner that they establish contact both in the case of longitudinal and transversal contact-connection or a mixture thereof. The switching devices 12a, 13a may contain electrical switching contacts or may also be, for example, devices which generate a signal which is generated by strain gauges, by piezo elements, by optical or magnetic, inductive or capacitive sensors and represents the predefined contact pressure.

Figure 4:
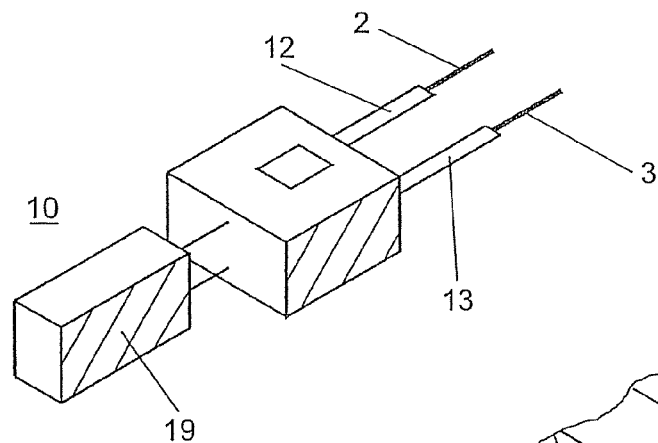
FIGS. 4a) and b) show perspective views of the device according to the invention, its structure and handling being shown.
Figure 4:
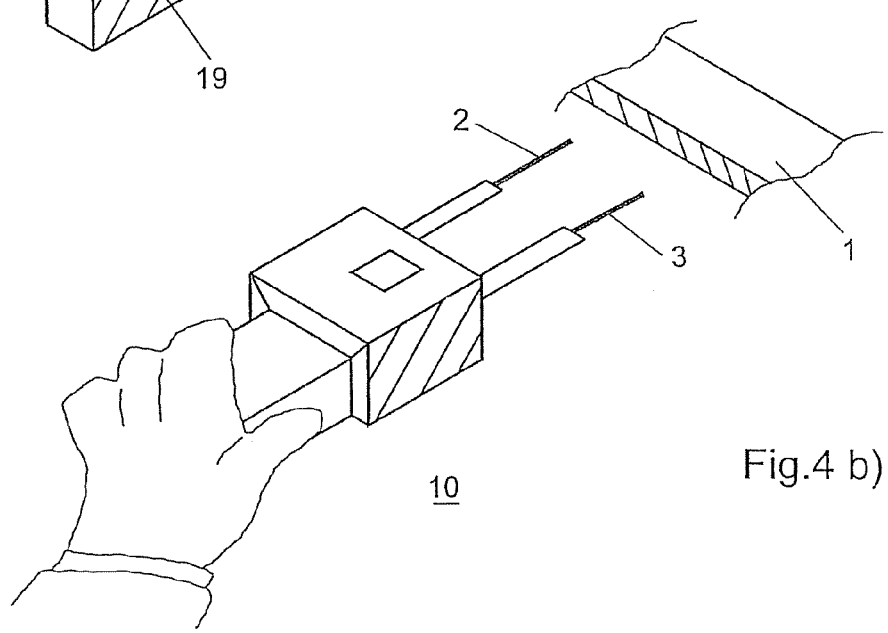

As shown in FIGS. 4a) and b), the test device of the exemplary embodiment illustrated is in the form of an instrument which can be manually operated and has a handle 19 for its handling. The instrument has its own current source 4 and is in the form of a small, lightweight but nevertheless robust instrument which is suitable for checking a large number of components in a short space of time. The measurement time for checking an individual component may be less than 0.5 seconds or even less than 0.3 seconds.

What is claimed is:

1. A device for checking the coating of light-metal parts, the device comprising:
    two contact electrodes, which are arranged on respective resilient probes, and which are placed onto the surface of the component to be tested under a certain contact pressure,
    an enabling device, which is coupled to the probes and generates an enable signal when the predefined contact pressure is reached, and
    a conductivity measuring device for measuring the conductivity of the surface of the component to be tested, the conductivity measuring device being coupled to the enabling device in order to pick up the enable signal, the conductivity measuring device measuring the conductivity of the surface of the component to be tested between the contact electrodes and, when the enable signal is present, generating an output signal which indicates the measured conductivity and distinguishing at least between a measured low conductivity value, which indicates a correct coating, and a measured high conductivity value, which indicates a lack of the coating.

2. The device according to claim 1, wherein the enabling device contains switching devices which are coupled to the resilient probes and are respectively switched when the predefined contact pressure is reached, and in that the enabling device generates the enable signal when both switching devices have been switched.

3. The device according to claim 2, wherein the probes are mounted or formed in a resiliently flexible manner and are coupled to the switching devices in such a manner that the switching devices are switched when the predefined contact pressure is reached.

4. The device according to claim 2, wherein the switching devices are formed in a resiliently flexible manner, are coupled to the probes and are switched when the predefined contact pressure is reached.

5. The device according to claim 2, wherein the switching devices contain electrical switching contacts.

6. The device according to claim 2, wherein the switching devices contain strain gauges.

7. The device according to claim 2, wherein the switching devices contain piezo elements.

8. The device according to claim 2, wherein the switching devices contain optical sensors.

9. The device according to claim 2, wherein the switching devices contain magnetic, inductive or capacitive sensors.

10. The device according to claim 1, wherein the measuring device is provided for the purpose of generating an acoustic output signal which indicates the measured conductivity.

11. The device according to claim 10, wherein the measuring device is provided for the purpose of generating the acoustic output signal with a pitch which differs depending on the measured conductivity.

12. The device according to claim 11, wherein the measuring device is provided for the purpose of using a low tone to indicate a low conductivity, which signifies a correct coating, and using a high tone to indicate a high conductivity, which signifies a lack of the coating.

13. The device according to claim 1, wherein the measuring device is provided for the purpose of generating an optical output signal which indicates the measured conductivity.

14. The device according to claim 1, wherein the measuring device is provided for the purpose of generating an electrical output signal which indicates the measured conductivity.

15. The device according to claim 1, wherein the device is provided in the form of an instrument which is manually operated and has a handle.

16. The device according to claim 15, wherein the device has its own current supply source.

17. The device according to claim 1, wherein the parts are aluminum components.

18. The device according to claim 1, wherein the parts have been coated by anodization.

19. The device according to claim 18, wherein the parts have been coated by TSA anodization.

* * * * *